US009636671B2

(12) United States Patent
Kilner et al.

(10) Patent No.: US 9,636,671 B2
(45) Date of Patent: May 2, 2017

(54) HOMOGENEOUS PROCESS FOR THE HYDROGENATION OF CARBOXYLIC ACIDS AND DERIVATIVES THEREOF

(75) Inventors: Melvyn Kilner, Wilton Gilbert (GB); Derek Vincent Tyers, Teesdale (GB); Simon Peter Crabtree, Durham Moor (GB); Michael Anthony Wood, Hilton (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 13/588,595

(22) Filed: Aug. 17, 2012

(65) Prior Publication Data
US 2013/0029831 A1    Jan. 31, 2013

Related U.S. Application Data

(60) Division of application No. 12/546,187, filed on Aug. 24, 2009, now abandoned, which is a continuation of application No. 10/513,290, filed as application No. PCT/GB03/01819 on Apr. 29, 2003, now Pat. No. 7,709,689.

(30) Foreign Application Priority Data

May 2, 2002   (GB) .................................. 0210143.4

(51) Int. Cl.
| C07C 27/04 | (2006.01) |
| B01J 31/24 | (2006.01) |
| B01J 31/40 | (2006.01) |
| C07C 29/149 | (2006.01) |

(52) U.S. Cl.
CPC ........... *B01J 31/2409* (2013.01); *B01J 31/24* (2013.01); *B01J 31/4023* (2013.01); *B01J 31/4046* (2013.01); *B01J 31/4053* (2013.01); *C07C 27/04* (2013.01); *C07C 29/149* (2013.01); *B01J 2231/641* (2013.01); *B01J 2531/0258* (2013.01); *B01J 2531/821* (2013.01); *B01J 2531/822* (2013.01); *B01J 2531/824* (2013.01); *B01J 2531/825* (2013.01); *B01J 2531/842* (2013.01); *B01J 2531/96* (2013.01); *Y02P 20/52* (2015.11); *Y02P 20/584* (2015.11)

(58) Field of Classification Search
CPC .... B01J 31/24; B01J 31/2409; B01J 31/4023; B01J 31/4046; B01J 31/4053; B01J 2531/842; B01J 2531/825; B01J 2531/824; B01J 2531/822; B01J 2531/641; B01J 2531/0258; B01J 2531/821; C07C 29/149; C07C 27/04; C07C 31/10; C07C 31/207; C07C 31/04
USPC .................. 502/20–56, 66, 74, 188
See application file for complete search history.

(56) References Cited

U.S. PATENT DOCUMENTS

| 3,852,346 A * | 12/1974 | Forster ..................... B01J 27/08 502/229 |
| 3,957,827 A | 5/1976 | Lyons |
| 4,021,463 A * | 5/1977 | Kummer et al. ............... 556/16 |
| 4,301,077 A | 11/1981 | Pesa et al. |
| 4,480,115 A | 10/1984 | McGinnis |
| 4,485,245 A | 11/1984 | Hsu et al. |
| 4,827,001 A | 5/1989 | Attig et al. |
| 4,892,955 A | 1/1990 | Wada et al. |
| 4,931,573 A | 6/1990 | Wada et al. |
| 5,021,589 A | 6/1991 | Wada et al. |
| 5,047,561 A * | 9/1991 | Miyazawa et al. ........... 549/325 |
| 5,077,442 A | 12/1991 | Hara et al. |
| 5,079,372 A | 1/1992 | Wada et al. |
| 5,107,053 A | 4/1992 | Wu |
| 5,118,825 A | 6/1992 | Wu |
| 5,420,306 A | 5/1995 | Noyori et al. |
| 5,580,991 A * | 12/1996 | Sugiyama et al. ............ 549/325 |
| 5,599,262 A | 2/1997 | Shih |
| 5,599,962 A | 2/1997 | Beatty et al. |
| 5,689,003 A | 11/1997 | Beatty et al. |
| 6,008,384 A | 12/1999 | Bockrath et al. |
| 6,133,477 A * | 10/2000 | Bruner ......................... 562/522 |

FOREIGN PATENT DOCUMENTS

| EP | 0055512 | 7/1982 |
| EP | 0420062 | 4/1991 |
| EP | 1077080 | 2/2001 |
| GB | 2092907 | 8/1982 |

(Continued)

OTHER PUBLICATIONS

Y, Hara et al., "Hydrogenatin Reaction of Carboxylic Anhydrides Catalyzed by a New and Highly Active Cationic Ruthenium Complex", Chemistry Letters (1991) pp. 553-554.
H-Inagaki et al., "Hydrogenation Reaction of Carbonyl Compounds Catalyzed by Cationic Ruthenium Complexes", Science and Technology in Catalysis (1994) pp. 327-330.
Grey et al., "Anionic Metal Hydride Catalysts. 2. Application to the Hydrogenation of Ketones, Aldehydes, Carboxylic Acid Esters, and Nitriles" J. Am. Chem. Soc. (1981) vol. 103, pp. 7536-7542.
Matteoli et al., "Structure and catalytic activity of phosphine-substituted ruthenium carbonyl carboxylates", Journal of Organometallic Chemistry 498 (1995) pp. 177-186.

(Continued)

*Primary Examiner* — Jennifer A Smith
(74) *Attorney, Agent, or Firm* — McDonnell Boehnen Hulbert & Berghoff

(57) ABSTRACT

A homogenous process for the hydrogenation of the carboxylic acids and/or derivatives thereof in the presence of a catalyst comprising ruthenium, rhodium, iron, osmium or palladium, and an organic phosphine is described in which the hydrogenation is carried out in the presence of at least about 1% by weight water. A process for regenerating a catalyst comprising ruthenium, rhodium, iron, osmium or palladium and an organic phosphine is also described in which the regeneration is carried out in the presence of hydrogen and water.

3 Claims, No Drawings

(56) References Cited

FOREIGN PATENT DOCUMENTS

| | | |
|---|---|---|
| JP | 2-72726 | 3/1990 |
| JP | 2-121976 | 5/1990 |
| JP | 2-200648 | 8/1990 |
| JP | 2-200680 | 8/1990 |
| JP | 2-207081 | 8/1990 |
| JP | 2-233674 | 9/1990 |
| JP | 2-235880 | 9/1990 |
| JP | 3-074377 | 3/1991 |
| JP | 3-083974 | 4/1991 |
| JP | 3-112973 | 5/1991 |
| JP | 3-141273 | 6/1991 |
| JP | 3-204870 | 9/1991 |
| JP | 4-091085 | 3/1992 |
| JP | 4-217636 | 8/1992 |
| JP | 6-107654 | 4/1994 |
| JP | 6-172338 | 6/1994 |
| JP | 7-033756 | 2/1995 |
| JP | 7-082260 | 3/1995 |
| JP | 20000344244 | 2/2000 |
| WO | 98/52891 | 11/1998 |

OTHER PUBLICATIONS

Teunissen et al., "Ruthenium catalysed hydrogenation of dimethyl oxalate to ethylene glycol", Chem. Commun., (1997) pp. 667-668.
Teunissen et al., Homogeneous ruthenium catalyzed hydrogenation of esters to alcohols, Chem. Commun. (1998) pp. 1367-1368.
Jones, C.W., "Applications of Hydrogen Peroxide and Derivatives", R&C Clean Technology Monographs pp. 13-23, Print publication date: Nov. 5, 1999.
Science Lab.com; "Material Safety Data Sheet Hydrogen Peroxide, 50%MSDS", pp. 1-7; Oct. 9, 2005.

* cited by examiner

HOMOGENEOUS PROCESS FOR THE HYDROGENATION OF CARBOXYLIC ACIDS AND DERIVATIVES THEREOF

This application is a divisional of U.S. application Ser. No. 12/546,187, filed Aug. 24, 2009, now abandoned which is a continuation of U.S. application Ser. No. 10/513,290, filed Jun. 20, 2005, now U.S. Pat. No. 7,709,698 which is a National Stage of International Application No. PCT/GB03/01819, filed Apr. 29, 2003, which claims priority to Great Britain Application No. 0210143.4, filed May 2, 2002.

BACKGROUND OF THE INVENTION

The present invention relates to a homogeneous process for the hydrogenation of carboxylic acids and/or derivatives thereof. More particularly it relates to a homogeneous hydrogenation process which can be carried out in the presence of water.

Many catalyst systems are known which are suitable for use in the hydrogenation of carboxylic acids, acid anhydrides, esters or amides. Traditionally such reactions are carried out using heterogeneous catalysts and often high temperatures and pressures. A disadvantage of these heterogeneous catalyst systems is that many are intolerant of acid feedstocks and therefore have limited use.

In order to overcome this problem, catalysts have been suggested for the hydrogenation of carboxylic acids and their derivatives based on ruthenium/phosphine systems. Examples of these catalyst systems include those described in U.S. Pat. No. 5,047,561, U.S. Pat. No. 5,079,372, U.S. Pat. No. 5,580,991, U.S. Pat. No. 5,077,442, U.S. Pat. No. 5,021,589, U.S. Pat. No. 4,931,573, U.S. Pat. No. 4,892,955, "Hydrogenation reaction of carboxylic anhydrides catalyzed by a new and highly active cationic ruthenium complex", Y-Hara et al Chem Lett (1991) 553, U.S. Pat. No. 3,957,827, U.S. Pat. No. 4,485,245 and U.S. Pat. No. 4,480,115 which are incorporated herein by reference.

However, whilst the systems described in these document provide processes which in general adequately enable hydrogenation reactions to be carried out, they do suffer from certain disadvantages and drawbacks. In particular, they require that the hydrogenation reaction is carried out in the absence of water since it is believed that any water present inhibits the catalyst or significantly reduces the rate of reaction. For example, in U.S. Pat. No. 5,047,561 an organic solvent is used and it is stated that the amount of water present should be controlled and should be no higher than 1% by weight. In "Hydrogenation reaction of carbonyl compounds catalyzed by cationic ruthenium complexes", H-Inagaki et al, Science and Technology of Catalysis (1994) 327 it is explained that the presence of water retards the hydrogenation reaction of succinic anhydride in the presence of a ruthenium trialkyl phosphine complexes in the presence of a promotor and that it is necessary to remove the water produced by hydrogenation in the gas stream and in U.S. Pat. No. 3,957,827 and U.S. Pat. No. 4,485,245 scavengers are used to remove any water produced in the reaction with the aim of improving yield and productivity.

Many of these known catalyst systems also require the presence of a promotor to increase the selectivity and activity of the ruthenium catalyst. Examples of this include U.S. Pat. No. 5,079,372 and U.S. Pat. No. 4,931,573 where reactions are carried out in the presence of an organic solvent and a metal selected from Group IVA, VA and III is required as a promotor.

Another example of the use of a promotor may be found in U.S. Pat. No. 5,077,442. In this case a phosphorous compound is used to promote selectivity and conversion. This document teaches that any water produced in the reaction is removed from the reaction zone as the presence of water is said to decrease selectivity and conversion.

Another suitable promotor described is a conjugate base of an acid and in this connection reference may be made to U.S. Pat. No. 5,021,589 and U.S. Pat. No. 4,892,955. In this latter case, it is noted that components of the catalyst system are susceptible to hydrolysis under the reaction conditions and that a hydrogen purge was required to remove water produced during the reaction.

Whilst these processes go some way to providing adequate catalyst systems, there is still a need for alternative process which allow for efficient hydrogenation of carboxylic acids and/or derivatives thereof with good conversion and selectivity to the desired products. Surprisingly, we have now established that the presence of water is not only not disadvantageous but indeed offers positive advantages.

SUMMARY OF THE INVENTION

Thus, according to the present invention there is provided a homogeneous process for the hydrogenation of carboxylic acids and/or derivatives thereof in the presence of a catalyst comprising:
  (a) ruthenium, rhodium, iron, osmium or palladium; and
  (b) an organic phosphine;
wherein the hydrogenation is carried out in the presence of more than 1% by weight water.

DESCRIPTION OF THE PREFERRED EMBODIMENTS

By "homogeneous process" we mean that the catalyst is dissolved in the solvent for the reaction and that at least some of the water present and at least some of the carboxylic acid and/or derivatives thereof must be in phase with the catalyst. Where excess water and/or carboxylic acid and/or derivatives thereof is present, the excess may form a separate phase to that comprising the catalyst. Additionally or alternatively, the product may form a separate phase.

By carboxylic acids and/or derivatives thereof, we mean any molecule containing a carboxylic acid functional group for example, carboxylic acids, dicarboxylic acids, polycarboxylic acids, hydroxy carboxylic acids, aromatic carboxylic acids, anhydrides, amides, esters, monoesters of dicarboxylic acids and mixtures thereof.

Where the carboxylic acid and/or derivative thereof is water soluble, the water may be present as the solvent for the reaction. Alternatively a solvent may be used. Where a solvent is used, the water will be present as an additive in the solvent or will be generated in situ. In another alternative arrangement, the acid or its derivative or the product of the reaction may be the solvent.

Where the carboxylic acid and/or derivative thereof is non-water soluble, such as for example for higher carbon content carboxylic acids and esters, the reactant or product may be the solvent for the reaction or an organic solvent may be used and the water may be present as an additive. In this case, it may be present in the solvent in an amount of from about 1% to the solubility limit of the water in the solvent. Additional water may be present in a separate aqueous phase.

In one alternative arrangement, the water may be produced in situ as a by-product of the hydrogenation. Where the water is generated in situ, if maximum benefits are to be achieved, the water should be generated within the first few cycles of the reaction. Where the water is to be generated in situ, an amount of water may be added initially to cover the system's requirement until sufficient water has been generated.

It will therefore be understood, that the process of the present invention offers substantial advantages over the prior art arrangements in that water need not be removed from any reactants prior to the start of the reaction and may even be the solvent. Further, any water produced in the reaction need not be removed from the reactor. By this means, the known processes are simplified which will have cost implications.

Further, we have found that the presence of water is beneficial in terms of catalyst stability. It is noted that in prior art systems, decarbonylation of, for example, the product alcohols or intermediate aldehydes occurs and the carbon monoxide formed strongly inhibits the catalyst. To overcome this it is usual, in prior art arrangements, for the carbon monoxide to be removed and a methanation unit to be included in the plant to deal with recycling of vent gas to the reactor. However, this is unnecessary in the process of the present invention.

Without wishing to be bound by any theory it is believed that the presence of the water allows a side reaction to occur in the hydrogenation reactor in which any carbon monoxide produced reacts with the water to form carbon dioxide and hydrogen via the water gas shift reaction. This carbon dioxide and hydrogen may be further reacted to form methane. These gases can be readily removed from the reaction system thereby reducing the costs of the hydrogenation process. Thus, this system not only provides a cost-effective hydrogenation process but also obviates the need to have a separate methanation unit in the recycling system for vent gases.

A further advantage of the present invention is that the removal of the carbon monoxide as detailed above allows for effective regeneration of the catalyst. Thus the process offers extended catalyst life which in turn improves the economics of the reaction.

The water gas shift reaction does require heat for its initiation. Where the carboxylic acid and/or derivatives thereof or the product of the hydrogenation is not thermally stable at the initiation temperature, the process of the present invention can be operated whereby the catalyst is allowed to be inhibited by the presence of generated carbon monoxide, the thermally unstable moiety is removed and the heat is then increased in the presence of the hydrogen such that the water gas shift reaction can operate to reactivate the catalyst for further reaction. By this means the process can be applied to a broad range of acids with prolonged catalyst life.

A still further advantage of the present invention is that there is no requirement to add buffer salts of the kind used in the prior art to stabilise the catalyst and further, promotors are not generally required and may, in some circumstances, even be deleterious. The reaction is preferably carried out in the absence of halides.

As described above, where the carboxylic acids and/or derivatives thereof are soluble in water, the water may act as the solvent. However, the method of the present invention may be conducted in the absence of a solvent, ie the starting material or reaction product may be a solvent for the reaction. However, if a solvent is used, any suitable solvent may be selected and examples of suitable solvents include, but are not limited to, diethyl ether, tetrahydrofuran, ethylene glycol dimethyl ether, dioxane, 2-propanol, 2-butanol, secondary alcohols, tertiary alcohols, or toluene with tetrahydrofuran and other ethers being particularly preferred.

The preferred catalyst of the present invention is a ruthenium/phosphine catalyst. The ruthenium is generally provided as a ruthenium salt although halides are not preferred. Suitable salts are those which can be converted to active species under the reaction conditions and include nitrates, sulphates, carboxylates, beta diketones, and carbonyls. Ruthenium oxide, carbonyl ruthenates and complex compounds of ruthenium, including hydridophosphineruthenium complexes, may also be used. Specific examples include, but are not limited to, ruthenium nitrate, ruthenium dioxide, ruthenium tetraoxide, ruthenium dihydroxide, ruthenium acetylacetonate, ruthenium acetate, ruthenium maleate, ruthenium succinate, tris-(acetylacetone)ruthenium, pentacarbonylruthenium, dipotassium tetracarbonyl-ruthenium, cyclo-pentadienyldicarbonyltriruthenium, tetrahydridedecacarbonyltetraruthenium, tetraphenylphosphonium, ruthenium dioxide, ruthenium tetraoxide, ruthenium dihydroxide, bis(tri-n-butylphosphine)tricarbonylruthenium, dodecacarbonyl-triruthenium, tetrahydridedecacarbonyltetraruthenium, tetraphenylphosphonium, undecacarbonylhydride-triruthenate.

The ruthenium compound may be present in any suitable amount. However, it is preferably present in an amount of from 0.0001 to 100 mol, preferably 0.005 to 5 mol, as ruthenium per liter of reaction solution.

Any suitable phosphine may be used. Compounds which provide tridentate, bidentate and monodentate ligands may be used. Where the metal is ruthenium, tridentate phosphines are particularly preferred. Examples of suitable phosphine compounds include trialkylphosphines, dialkylphosphines, monoalkylphosphines, triarylphosphines, diarylphosphine, monoarylphosphines, diarylmonoalkyl phosphines and dialkylmonoaryl phosphines. Specific examples include but are not limited to tris-1,1,1-(diphenylphosphinomethyl)methane, tris-1,1,1-(diphenylphosphinomethyl)-ethane, tris-1,1,1-(diphenylphosphinomethyl) propane, tris-1,1,1-(diphenylphosphino-methyl)butane, tris-1,1,1-(diphenylphosphino-methyl)-2-ethane-butane, tris-1,1,1-(diphenylphosphinomethyl)2,2-dimethylpropane, tris-1,3,5-(diphenylphosphinomethyl)cyclohexane, tris-1,1,1-(dicyclohexylphosphinomethyl)ethane, tris-1,1,1-(dimethylphosphinomethyl)ethane, tris-1,1,1-(diethylphosphinomethyl)ethane, 1,5,9-triethyl-1,5-9-triphosphacyclododecane, 1,5,9-triphenyl-1,5-9-triphosphacyclododecane, bis(2-diphylephosphinoethyl) phenylphosphine, bis-1,2-(diphenyl phosphino)ethane, bis-1,3-(diphenyl phosphino)propane, bis-1,4-(diphenyl phosphino)butane, bis-1,2-(dimethyl phosphino)ethane, bis-1,3-(diethyl phosphino)propane, bis-1,4-(dicyclohexyl phosphino)butane, tricyclohexylphosphine, trioctyl phosphine, trimethyl phosphine, tripyridyl phosphine, triphenylphosphine with tris-1,1,1-(diphenylphosphinomethyl)ethane being particularly preferred.

The phosphine compound may be present in any suitable amount. However, it is preferably present in an amount of from 0.0001 to 100 mol, preferably 0.005 to 5 mol, as ruthenium per liter of reaction solution.

Any suitable reaction temperature may be used. However, in the process of the present invention, particular advantages may be noted if the hydrogenation is carried out at temperatures in the region of from about 150° C. to about 350° C.

Any suitable pressure may be used with a reaction pressure of from about 250 psig to about 2000 psig, preferably of from 800 psig to 1200 psig and most preferably 1000 psig.

The process may be carried out either in a batch system or in a continuous system. However, it will be understood that the process of the present invention is particularly suitable for use in a continuous system since the catalyst is not poisoned by carbon monoxide or if poisoning in this way occurs, the catalyst can be regenerated by reaction with the water.

Where the catalyst is removed from the reactor, for example, with a product removal stream, it may be recycled by any suitable means to the reactor.

It will be understood that the process of the present invention relating to regenerating the catalyst may be applied to catalysts which have been inhibited during processes carried out under conventional processes such as those described in the prior art and in particularly in the documents detailed above. Thus, according to a second aspect of the present invention there is provided a process for regenerating a catalyst comprising:

(a) ruthenium, rhodium, iron, osmium or palladium; and
(b) an organic phosphine;

wherein the regeneration is carried out in the presence of hydrogen and water, preferably via the water gas shift reaction.

The regeneration may be carried out at any suitable temperature with temperatures of from about 150° C. to about 350° C. being preferred.

The present invention will now be described with reference to the following examples which are not intended to be limiting on the scope of the invention.

Example 1 illustrates that maleic acid may be successfully hydrogenated in the presence of water.

Ruthenium(III)acetylacetonate (0.46 mmols, 0.181 g) and 1,1,1 tris(diphenylphosphinomethyl)ethane (triphos) (6.1 mmols, 0.38 g), water (71 g) and maleic acid (ex Fluka, 20.2 g) were transferred into a 300 ml Hastelloy Parr autoclave. This was sealed and purged with hydrogen before being pressurised to 700 psig with hydrogen and heated to 241° C. Once 241° C. had been achieved, the reactor was topped up with hydrogen to 1000 psig and this pressure was maintained throughout the reaction via a mass flow meter, which recorded the amount of hydrogen added. At the end of the reaction the hydrogen supply was isolated and the reactor cooled. At room temperature the headspace gas was analysed using a Pye-Unicam refinery gas analyser, before being vented. The product was removed from the reactor and weighed (91.42 g). The maleic conversion was determined by titration of the liquid product against 0.1M sodium hydroxide. (>99.9%). The water and organic analysis was determined using an HP gas chromatograph equipped with a micro TCD (wt %): water (86.52), propanol (0.84), tetrahydrofuran (7.02) propionic acid (0.14), γ-butyrolactone (2.47) butanediol (2.83); giving an overall molar selectivity to tetrahydrofuran of 51.1%, to γ-butylractone of 15.1%, and to butanediol of 16.5%, others 17.3%.

Comparative Example 1 illustrates the effect of the presence of insufficient water to maintain the activity of the reaction.

Example 1 was repeated except that the water and maleic acid were replaced by methyl propionate (64 g) and the reaction conducted at 164° C. After 15 hours, at the end of the reaction, 59.4 g of product was recovered as a yellow solution with a small amount of yellow solid. The solution was analysed and found to be (wt %) methanol (7.15), water (2.10), propanol (8.46), methyl propionate (75.62), propionic acid (0.25) propyl propionate (4.99); giving a selectivity to propanol of 75.2 mol % and to propyl propionate of 23.0 mol %. The molar conversion was 16.9%. It can therefore be seen that the absence of added water, insufficient water is generated in the initial hydrogenation of the ester to allow the reaction to continue to completion. The solid component from this reaction was analysed and found to be [Ru(triphos)(CO)(H)$_2$] and thus it was concluded that the catalyst had been poisoned with the carbon monoxide.

Comparative Example 2 demonstrates that in the absence of water the isolated solid is not active for the reduction and in particular that in the absence of added water the deactivated catalyst [Ru(triphos)(CO)H$_2$] is effectively inactive.

Several reactions were performed in the manner of Comparative Example 1 and the solid product, [Ru(triphos)(CO)(H)$_2$] was collected, washed and dried (0.2263 g) then returned to the reactor with a fresh charge of methyl propionate (17.7 g) and isopropanol (38.6 g). This was then heated at 164° C. for 15.5 hours, at the end of this time the reactor was cooled and 52.2 g of product recovered. The liquid product was analysed and found to be methanol (1.04), isopropanol (73.02), water (0.62), propanol (1.23), methyl propionate (23.53) and propyl propionate (0.08); giving molar selectivities of 92.5% for propanol and of 3.1% for propyl propionate and a molar conversion of 7.3%

Examples 2 and 3 demonstrate hydrogenation of an ester in the presence of water. These examples demonstrate that in the presence of water ester hydrogenation proceeds to effectively 100% conversion.

In Example 2, Example 1 was repeated using 48.64 g of water and 23.26 g of dimethyl maleate as feed. The reaction was conducted at 191° C. After 53 hours the liquid and gaseous products were cooled and the liquid product analysed by gas chromatography and found to be off gas (mol %) hydrogen (98.9), carbon monoxide (0.08), methane (0.01) and carbon dioxide (0.113) liquid (wt %) methanol (15.37) water (67.11) tetrahydrofuran (27.43), γ-butyrolactone (0.333) and butanediol (12.29) giving a molar conversion of 99.5 mol % and a selected activity to desired products of (mol %) tetrahydrofuran (27.43) γ-butylractone (1.88) butanediol of (66.24).

In Example 3, Example 1 was again repeated using 48.4 g of water and 20.1 g of methyl propionate as feed. The reaction was conducted at 192° C. After 15 hours the reactor was cooled and the liquid product analysed by gas chromatography and found to be methanol (10.25) water (70.75) propanol (18.27) methyl propionate (<0.1) propionic acid (<0.1) propyl propionate (<0.1), giving a molar selectivity and conversion of >99.5%

Example 4 illustrates the reactivation of the deactivated catalyst by the use of water In particular to establish that the effect of water on the deactivated catalyst is to cause a change in the nature of the species and to cause carbon dioxide to be released.

A sample of the deactivated catalyst, [Ru(triphos)(CO)H$_2$] (0.3536 g), deionised water (49.05 g) and tetrahydrofuran (17.47 g) were loaded into the autoclave used previously, which was then sealed, purged with hydrogen, pressurised with hydrogen to 714 psig then heated to 193° C. for 15.5 hours. At the end of this time the reactor was cooled and the head space gas purged through a CO$_2$ Draeger tube, this slowly turned pale blue indicating the presence of CO$_2$. the solution from the reaction was analysed by proton decoupled phosphorus NMR and found to be different when compared with the spectrum obtained from [Ru(triphos)(CO)H$_2$] dissolved in tetrahydrofuran.

The [Ru(triphos)(CO)H$_2$] in tetrahydrofuran gives a characteristic doublet and triplet at 25 and 34 ppm respectively. In the case of the sample that had been heated under hydrogen in water, these signals had completely disappeared, to be replaced by a complex array of other signals illustrating that the deactivated species had been removed.

Example 5 illustrates the direct hydrogenation of a simple (propionic) acid, producing sufficient water in-situ to maintain the reaction. This further demonstrates that acids may be hydrogenated directly with the water produced in the reaction causing the in-situ reactivation of the catalyst.

The method of Example 1 was repeated except that the water and maleic acid were replaced with propionic acid (69.7 g, 98% pure ex Aldrich). After 5 hours at temperature, the reactor was cooled to room temperature and the off gas analysed and found to contain (mol %) carbon dioxide (0.29), methane (0.95), carbon monoxide (0.73), ethane (2.21) and propane (0.31). The liquid product was recovered from the autoclave and found to be two phase, 64.8 g of an upper (organic layer) and 5.6 g of a lower (aqueous layer). These layers were analysed and found to be (wt %) upper, water (17.0), propanol (38.59), propionic acid (11.9), propyl propionate (31.9); lower water (83.66) propanol (11.73), propionic acid (3.47) and propyl propionate (0.6). These gave an overall molar selectivity to propanol of 64.5%, propyl propionate 27.0% which in itself would afford 1-propanol and a conversion of 79.3%.

Example 6 relates to the hydrogenation of fumaric acid and demonstrates that other diacids may be hydrogenated.

The method of Example 1 was repeated except that the maleic acid was replaced with fumaric acid (20.3 g, 98%). After 12 hours at temperature, the reactor was cooled to room temperature The liquid product was recovered from the autoclave (90.1 g) and analysed (wt %), water (82.74), propanol (0.13), propionic acid (0.04), tetrahydrofuran (6.00), γ-butylractone (2.19), butanediol (8.35); giving an overall molar selectivity to tetrahydrofuran of 40.0%, γ-butyrolactone of 12.2%, and to butanediol of 44.53%. Titration against 0.01M sodium hydroxide gave >98% conversion of the fumaric acid Example 7 illustrates the direct hydrogenation of lactic acid. This further demonstrates that organic acids may be hydrogenated.

The method of Example 1 was repeated except that the water and maleic acid were replaced with lactic acid, 85+%, solution in water, (93.34 g, ex Aldrich). After 6 hours at 190° C., the reactor was cooled to room temperature. The liquid product was recovered from the autoclave and found to be single phase, 94.47 g. The analysis found (wt %): water (26.25), and propylene glycol (72.74) which represented a conversion of >99.5%.

Example 8 illustrates the direct hydrogenation of an acid in the presence of a solvent. The method of Example 1 was repeated except that maleic acid was replaced with succinic acid (20.03 g), 1-methyl-2-pyrrolidinine (20.61 g) was included as a solvent and the amount of water (49.86 g) included, was reduced. At the end of the reaction the products were analysed and found to be (wt %): water (61.43), propanol (0.14), tetrahydrofuran (3.69), propionic acid (0.15), -butyrolactone (3.87), butanediol (5.22); giving an overall selectivity to tetrahydrofuran of 30.49%, to -butyrolactone of 26.81%, and to butanediol of 34.57%, and a conversion of 99%.

Example 9 illustrates the direct hydrogenation of an anhydride in accordance with the present invention The method of Example 5 was repeated except that propionic anhydride (39.23 g) and propionic acid (33.9 g) were used as feed. After 5 hours at temperature, the reactor was cooled to room temperature and the off gas analysed and found to contain (mol %) carbon dioxide (0.29), methane (0.95), CO (0.73), ethane (2.21), propane (0.31). The liquid product was recovered from the autoclave and found to be two phase, 73.2 g of an upper (organic layer) and 1.8 g of a lower (aqueous layer). These layers were analysed and found to be (wt %) upper, water (15.91), propanol (40), propionic acid (9.54), propyl propionate (33.88); lower water (63.25) propanol (21.89), propionic acid (4.59), propyl propionate (10.15). These gave an overall molar selectivity to propanol of 65.8%, propyl propionate 28.7% and a conversion of 80.87%.

Example 10 illustrates the direct hydrogenation of an amide in accordance with the present invention. It also illustrates that the catalyst is stable in the presence of nitrogen containing compounds such as ammonia and amines The method of Example 5 was repeated at 164_C, except that the propionic acid was replaced by propionamide (20.14 g), water, 20.26 g and tetrahydrofuran (solvent, 44.22 g). After 14 hours the reactor was cooled and vented and the contents analysed (area %) water+ammonia (9.81), propanol (10.57), tetrahydrofuran (53.76), dipropylamine (0.57) propyl propionate (1.32) propanamide (15.92) N-propyl propanamide (7.33).

Examples 11 to 20 demonstrate that whilst tris-1,1,1-diphenylphosphinomethyl)ethane is the preferred phosphine compound under these conditions, other phosphines are also suitable.

The method of Example 5 was repeated except that the tris-1,1,1-diphenylphosphinomethyl)ethane was replaced by a variety of other phosphines in various ruthenium:phosphine ratios. the results are summarised in Table 1

TABLE 1

| Example No. | phosphine compound | phosphine:ruthenium ratio | Conversion (mol %) | Selectivity (propanol + propyl propionate) (mol %) |
|---|---|---|---|---|
| 11 | tris-1,1,1-diphenylphosphinomethyl)ethane | 1 | 76.4 | 93.7 |
| 12 | Triphenylphosphine | 1.01 | 11.6 | 40.4 |
| 13 | Triphenylphosphine | 6 | 8.8 | 40.7 |
| 14 | Tricyclohexyl-phosphine | 3.09 | 16.0 | 68.2 |
| 15 | Tricyclohexyl-phosphine | 6.02 | 21.0 | 87.2 |
| 16 | Trioctyl phosphine | 6.1 | 39.3 | 89.0 |

TABLE 1-continued

| Example No. | phosphine compound | phosphine:ruthenium ratio | Conversion (mol %) | Selectivity (propanol + propyl propionate) (mol %) |
|---|---|---|---|---|
| 17 | 1,2 bis(diphenylphosphino)ethane | 2 | 24.8 | 81.5 |
| 18 | 1,2 bis(diphenylphosphino)ethane | 1 | 14.3 | 67.0 |
| 19 | 1,2 bis(diphenylphosphino)propane | 1 | 10.0 | 54.6 |
| 20 | 1,2 bis(diphenylphosphino)propane | 2 | 16.7 | 79.1 |

Comparative Example 3 demonstrates the unsuitability of a catalyst system comprising phosphine plus a strong acid promoter under the conditions preferred in this invention. This demonstrates that under these conditions the addition of strong acids is detrimental to the reaction and the strong acid can itself be reduced. Example 14 was repeated except that two molar equivalents of p-toluene sulphonic acid monohydrate were added. At the end of the reaction when the products were analysed, a sulphurous odour was detected indicative of $H_2S$ and the conversion had fallen to 10.2 mol % and the selectivity to propanol and propyl propionate to 68.2%.

Comparative Example 4 demonstrates that under the preferred reaction conditions the addition of sodium salts of strong acids is detrimental to the reaction reducing both the conversion and the selectivity. Example 1 was repeated except that two molar equivalents of sodium-p-toluene sulphonate were added. At the end of the reaction a white solid (succinic acid, 13.9 g) was recovered and the liquid products (82.5 g) were analysed by gas chromatography and found to be (wt %): water (95.90), propanol (0.10), tetrahydrofuran (0.09), propionic acid (1.478)-butyrolactone (1.67), butanediol (0.38); giving an overall selectivity to tetrahydrofuran of 2.43%, to -butyrolactone of 38.25%, and to butanediol of 8.26%. The conversion had fallen to 33.49 mol %.

Example 21 relates to catalyst recycle and demonstrates the recyclability of the ruthenium-phosphine catalyst.

The method of Example 5 was repeated except that the reaction was conducted at 241° C. for 4 hours. At the end of the reaction, the product liquor was placed in a rotary evaporator and reduced down to a minimal volume (~5 mls) at 70-80° C. and 60 Torr. The overheads were then analysed for acid conversion. The residual solution containing the catalyst was returned to the autoclave and made up to a total weight of 70 g with propionic acid and the reaction repeated. The results are summarised in Table 2 below. For recycle number seven the catalyst was not returned to the autoclave, instead 70 g of propionic acid was used on its own to demonstrate that the activity was not due to the precipitation of ruthenium on the reactor walls etc.

TABLE 2

| Recycle Number | Conversion (mol %) |
|---|---|
| 0 | 42 |
| 1 | 46 |
| 2 | 44 |
| 3 | 46 |
| 4 | 56 |
| 5 | 46 |
| 6 | 51 |
| 7 | 0 blank run |
| 8 | 44 |

It can therefore be seen that the conversion rate is maintained during recycle.

The invention claimed is:

1. A process for regenerating a catalyst comprising:
   forming a reaction mixture comprising water and a catalyst deactivated or poisoned by carbon monoxide, wherein the deactivated or poisoned catalyst comprises:
   (a) ruthenium, rhodium, iron, osmium or palladium; and
   (b) an organic phosphine; and
   regenerating the deactivated or poisoned catalyst in the presence of hydrogen, and at a temperature of from about 150° C. to about 350° C., via the water gas shift reaction;
   wherein the regenerating is carried out in the absence of halide.

2. The process of claim 1, wherein the temperature ranges from greater than 150° C. to about 350° C.

3. A process for regenerating a catalyst comprising:
   forming a reaction mixture substantially free of halide and comprising water and a catalyst deactivated or poisoned by carbon monoxide, wherein the deactivated or poisoned catalyst comprises:
   (a) ruthenium, rhodium, iron, osmium or palladium; and
   (b) an organic phosphine; and
   regenerating the deactivated or poisoned catalyst in the presence of hydrogen, and at a temperature of from about 150° C. to about 350° C., via the water gas shift reaction.

* * * * *